United States Patent [19]

Bunegin et al.

[11] Patent Number: 4,995,401
[45] Date of Patent: Feb. 26, 1991

[54] DEVICE FOR MEASURING ANTERIOR FONTANELLE PRESSURE

[75] Inventors: Leonid Bunegin; Maurice S. Albin, both of San Antonio, Tex.

[73] Assignee: Board of Regents, The University of Texas System, Austin, Tex.

[21] Appl. No.: 160,870

[22] Filed: Feb. 26, 1988

[51] Int. Cl.$^5$ ............................................. A61B 5/00
[52] U.S. Cl. .................................. 128/748; 128/774; 128/782
[58] Field of Search ............... 128/748, 774, 782, 672, 128/677, 715, 773, 678

[56] References Cited

U.S. PATENT DOCUMENTS

| | | | |
|---|---|---|---|
| 2,039,337 | 5/1936 | Nolan | 128/678 |
| 2,583,941 | 1/1952 | Gordon, Jr. | 128/715 X |
| 2,799,270 | 6/1957 | Rodbard | 128/678 |
| 3,123,068 | 3/1964 | Bigliano | 128/672 |
| 3,184,960 | 5/1965 | Murr et al. | |
| 3,299,882 | 1/1967 | Masino | |
| 3,359,789 | 12/1967 | Forse | |
| 3,534,733 | 10/1970 | Phipps | 128/643 |
| 3,593,704 | 7/1971 | Schwab | 128/687 |
| 3,658,054 | 4/1972 | Iberall | 128/672 |
| 3,704,708 | 12/1972 | Iberall | 128/680 |
| 3,811,429 | 5/1974 | Fletcher et al. | |
| 4,265,252 | 5/1981 | Chubbuck et al. | |
| 4,281,667 | 8/1981 | Cosman | 128/748 |
| 4,312,361 | 1/1982 | Nicholson et al. | 128/748 |
| 4,462,409 | 7/1984 | Pace et al. | |
| 4,502,491 | 3/1985 | Ender et al. | |
| 4,559,953 | 12/1985 | Wright et al. | 128/773 X |
| 4,610,256 | 9/1986 | Wallace | 128/673 X |
| 4,672,976 | 6/1987 | Kroll | 128/715 |
| 4,777,961 | 10/1988 | Saltzman | 128/773 X |

FOREIGN PATENT DOCUMENTS

| | | | |
|---|---|---|---|
| 1007653 | 3/1983 | U.S.S.R. | 128/687 |
| 2120901 | 12/1983 | United Kingdom | 128/715 |

OTHER PUBLICATIONS

The Fontanelle Tonometer: A Noninvasive Method for Measurement of Intracranial Pressure; Menke et al., J. Pediatrics, 100: 960-963 (1982).
Continuous and Intermittent Measurement of Intracranial Pressure by Ladd Monitor; Walsh and Logan, J. Pediatrics, 102: 439-442 (1983).
Measurement of Intracranial Pressure Using the Ladd Intracranial Pressure Monitor, Hill et al., J. Pediatrics, 98: 974-976 (1981).
Effect of Application Force on Noninvasive Measurements of Intracranial Pressure; Horbar et al., Pediatrics, 66: 455-457 (1980).
Comparison of Noninvasive and Direct Measurements of Intracranial Pressure; Myerberg et al., Pediatrics 65: 473-476 (1980).
Non-Invasive Method for Measuring Intracranial Pressure in Normal Newborn Infants; Robinson et al., Develop. Med. Chil Neurol.; 19: 305-308 (1977).
A Simple Noninvasive Technique of Measuring Intracranial Pressure in the Newborn; Vidyasagar et al., Neonatology Supplement, pp. 957-961.
The Fontogram: A Noninvasive Intracranial Pressure Monitor; Salamon et al., Pediatrics 60: 721-725 (1977).
Methods of Measuring Intracranial Pressure via the Fontanelle Without Puncture; Wealthall and Smallwood; J. Neurol. Neurosurg. Psych. 37: 88-96 (1974).

*Primary Examiner*—Max Hindenburg
*Assistant Examiner*—John P. Lacyk
*Attorney, Agent, or Firm*—Arnold, White & Durkee

[57] ABSTRACT

The present invention relates to a device for measuring anterior fontanelle pressure. A particular embodiment of this device comprises a rigid housing having an opening at its base end adapted for engaging a cranium and an aperture adapted to receive means for sensing pressure. The device may also include a flexible membrane disposed over the opening and adapted for engaging an anterior fontanelle. In this embodiment, the housing and membrane cooperate to define a cavity adapted to receive a fluid.

25 Claims, 5 Drawing Sheets

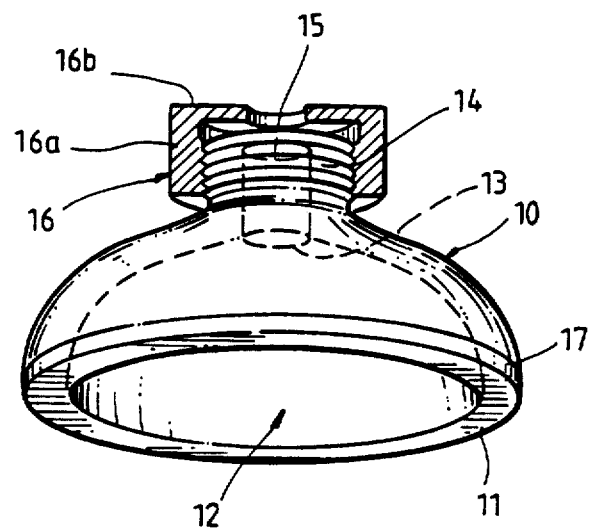
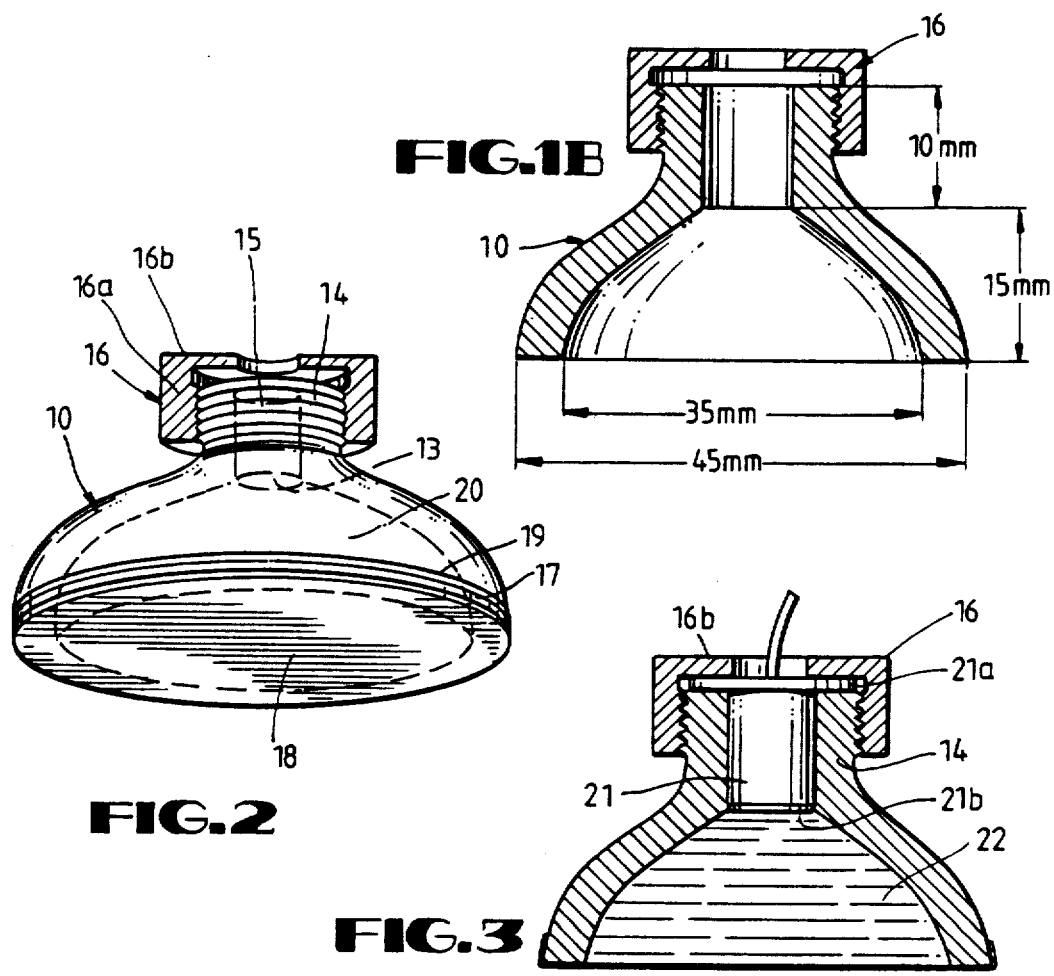

DEVICE FOR MEASURING ANTERIOR FONTANELLE PRESSURE

BACKGROUND OF THE INVENTION

A. Field of the Invention

The present invention relates to a device suitable for use in an anterior fontanelle pressure sensing system. This device allows one to make rapid and accurate measurements of the anterior fontanelle pressure of an infant using a noninvasive technique.

B. Description of the Related Art

The importance of measuring intracranial pressure in infants afflicted with certain pediatric disorders, such as Reye Syndrome, head injuries, hydrocephalus, and subarachnoid hemorrhage is being increasingly appreciated. However, invasive measurement techniques, for example, intraventricular catheters, subdural or epidural strain gauges, or telemetric devices are not well suited for routine monitoring of intracranial pressure in the infant. The first three create a potential for infection and the fourth would require major surgery to implant and remove the device.

Therefore, in recent years, considerable attention has been paid to the development of a noninvasive approach for evaluating intracranial pressure in newborns and infants. Instrumentation for estimating neonatal intracranial pressure has generally been designed to take advantage of the anterior fontanelle window of the newborn cranium. The anterior fontanelle is present at birth and closes between the ages of one and two years. The anterior fontanelle is a quadrangular defect bordered by the junction of the coronal, sagittal, and metopic sutures. Thus, in the face of increased intracranial pressure, the infant's brain may bulge into the anterior fontanelle and quantifications of this pressure increase is a noninvasive means of determining the magnitude of the pressure rise. Unfortunately, the devices of the prior art have met with limited acceptance because of a lack of consistent correlation to intracranial pressure; high sensitivity of transducer output to patient position and motion; lack of continuous monitoring capability in some designs; inability to correct for zero drift; the inability to calibrate in situ; and poor reproducibility following successive reapplications of the sensor to a given fontanelle.

The two devices that have been predominately used for anterior fontanelle pressure measurement are the aplanation transducer and the fiberoptic sensor.

The aplanation devices generally comprise a circular guard ring or baseplate (a plane surface) surrounding a pressure-sensitive plunger. When the guard ring or baseplate is placed against a membrane distended by pressure, the membrane will bulge through any hole in the surface When the plunger is placed in the hole and a force applied to it so that the end of the plunger is in the same plane as the baseplate, the pressure exerted by the plunger will theoretically be the same as that within the membrane Unfortunately, aplanation devices are typically motion sensitive, requiring minimal patient positional changes Also, these devices have no means for in situ calibration or baseline correction.

The fiberoptic sensor consists of a pressure sensitive sensor membrane with a miniature mirror mounted on its surface. Three fiberoptic columns are contained in a pneumatic tube connecting the sensor to a monitor The monitor transmits light to the sensor mirror via a central efferent optical fiber and compares the amount of reflected light carried back by the vertically flanking afferent fibers. A bellows systems can adjust the air pressure in the pneumatic tube in such a way that the sensor mirror is central and hence an equal amount of light is reflected back by the afferent fibers When the pressure acting on the contact surface of the sensor tilts the mirror, uneven reflection of light is fed back to the monitor. In response, the monitor balances the air pressure in the pneumatic tube to equalize the pressure on the transducer surface. The air pressure required to keep the mirror properly balanced is continuously displayed on the digital screen and a pen recorder simultaneously transcribes this pressure.

A disadvantage of this system is that sensor output is often affected by pressure with which the device is applied to the anterior fontanelle. Minimizing this problem requires meticulous attention to the application of the sensor, and reapplication of the sensor is required, often after only one or two hours.

Moreover, in most studies utilizing devices of the prior art to measure anterior fontanelle pressure, particularly the fiberoptic sensor, it appears that the sensor was applied to the fontanelle with prior knowledge of the intracranial pressure as measured by a ventricular catheter In such a case, it would often pose no problem to adjust the application force for good initial correlation. However, correlations between intracranial pressure and anterior fontanelle pressure following blind applications of either the fiberoptic sensor or aplanation devices have not been reported Therefore, usefulness of the prior art devices appears to be limited in that reproducible correlations between anterior fontanelle pressure and intracranial pressure upon blind application of the transducer have not been demonstrated. In addition, present designs have not provided any means by which transducer drift can be assessed in situ or baseline changes corrected following patient repositioning.

The problems enumerated in the foregoing are not intended to be exhaustive but rather are among many which tend to impair the effectiveness of devices presently employed to measure anterior fontanelle pressure in the infant. Although other noteworthy problems may also exist, those presented above demonstrate that the monitors used to monitor anterior fontanelle pressure have not been altogether satisfactory and illustrate that there is currently a great need for improved devices.

SUMMARY OF THE INVENTION

In accordance with the recognized need for an improved device for measuring intracranial pressure in the infant noninvasively, it is a general object of the invention to provide an anterior fontanelle monitoring system which includes a pressure sensing device which minimizes or reduces the problems of the type described above.

Therefore, in accordance with a general embodiment of the present invention, there is provided a pressure sensing device comprising a rigid housing having an opening at its base end adapted for engaging a cranium, and an aperture, typically located at its apical end, adapted to receive a pressure sensor.

In a further embodiment, there is provided a device comprising a rigid housing as described above, but additionally having a flexible membrane disposed over the opening. This membrane is adapted for engaging an anterior fontanelle and the housing and membrane cooperate to define a cavity that is adapted to receive a fluid. In yet further embodiments, there is a fluid filling the cavity and means for detecting fluid pressure changes within the cavity.

More particular embodiments relate to particular characteristics of the device. For example, in particular embodiments, the housing is described as having certain dimensions, for example, walls about 5 millimeters thick, or an opening in the base end of the housing about 35 millimeters in diameter. Of course, it will be appreciated that the outside base diameter of a housing constructed in this manner, would be about 45 millimeters. It is also preferred that the distance from a plane defined by the base end of the housing, or from the housing membrane if one is so provided, to the aperture located at the apex of the housing is about 15 millimeters.

In additional embodiments, the housing is constructed of a particular material, such as plastic, since this material is both durable and inexpensive to produce. Those of skill in the art will note that many types of plastic materials are likely to be suitable and include acrylic, polyvinyl chloride, and polycarbonate. However, as those of skill in the art will recognize, a number of other materials could be easily substituted.

In yet other embodiments, the housing is constructed in the form of a dome. It should be pointed out, that the term "domed housing" used by the inventors, may be defined as a housing, such as that shown in FIGS. IA and IB, 2 or 3, for example, that encloses a domed or conical cavity. That is, the term "domed housing" refers not only to a housing having an external shape in the form of a dome, but also, and more particularly, refers to a housing having an internal surface or cavity with the form of a dome or cone.

In a yet further embodiment, the aperture is positioned opposite the enlarged opening of the base end. Thus, where the housing is domed, the aperture will usually be positioned at the apex of the dome.

In still a further embodiment, the opening at the base end of the housing is defined as being equal to or greater than the circumference of an infant fontanelle. In an additional embodiment, the base end of the housing is adapted to engage the cranium of an infant circumferential to the anterior fontanelle. For purposes of the present invention, circumference of a fontanelle may be determined by measuring the circumference of the fontanelle at the cranial bone margin. Of course, as fontanelle sizes may vary somewhat from infant to infant, it will generally be desirable to construct the device such that the circumference of the fontanelle reflects the average or mean fontanelle size. Accordingly, fontanelle measurements of a number of infants can be obtained and averaged and the device constructed accordingly to the mean circumference obtained Of course, the fontanelle is generally more oval than circular and the terms "circumference" and "circumscribed" should not be construed to mandate a circular opening. A housing constructed according to either of the above embodiments is believed to be desirable, since when the housing is centered over the anterior fontanelle, the base end of the housing will be positioned over the scalp covering the cranial bones.

In addition, a more particular embodiment of the invention is directed towards a housing wherein the aperture comprises an external collar defining a port, a retainer cap having an annular sidewall and a top wall extending radially inward to define an opening in the cap, and means for engaging the outer surface of the collar with the inner surface of the annular wall of the retainer cap so as to facilitate sandwiching a member of the pressure sensing means between the upper surface of the collar and the internal surface of the top surface of the retainer cap.

Yet further embodiments are directed toward instrumentalities for mounting the device on the head of an infant. Although a number of mounting devices, for example, tape or elastic bandages, may be suitable in some cases, a preferred mounting device comprises a harness having elastic straps.

Further embodiments relate to the flexible membrane and its attachment to the housing. For example, in one further embodiment the flexible membrane comprises a silicon membrane In a preferred embodiment, the flexible membrane is affixed to the housing with an adhesive In yet a further embodiment, the device comprises an O-ring adapted for attaching the membrane to the housing.

Other embodiments relate to the fluid filling the housing cavity As those of skill in the art will appreciate, a number of suitable fluids may be used. The only requirement is that the fluid be relatively incompressible, for this reason, liquids are preferred and particularly preferred are sterile aqueous liquids such as distilled water or physiological saline or nonaqueous fluids such as liquid silicon.

As stated above, in some embodiments, the device will also comprise a mechanism for sensing pressure In a preferred embodiment, the pressure sensing mechanism will comprise a pneumatic switch. The pneumatic switch described in U.S. Pat. No. 4,312,361 is particularly preferred. However, other pressure sensing mechanisms such as strain gage or fiberoptic transducers may also be used with the present invention.

In another preferred embodiment, a pressure sensing element of the pressure sensing device will be disposed in an aperture in the housing, so that this element communicates with the fluid in the cavity of the housing.

Finally, the invention relates to a method for measuring intracranial pressure This method generally comprises providing a device enclosing a fluid filled cavity, said device having a rigid housing with a flexible membrane window, and means for sensing pressure The pressure sensing means communicates with the fluid in the cavity. The device is applied to the cranium of an infant in a manner such that the flexible membrane lies adjacent to the skin covering the anterior fontanelle, the rigid housing is supported by the cranium, and deformation of the skin covering the fontanelle causes a corresponding deformation of the flexible membrane and thereby changes the fluid pressure within the cavity. The fluid pressure changes within the cavity are detected with the pressure sensor.

A more specific embodiment relates to the pressure sensor. In this embodiment, the pressure sensor has a rigid casing defining a bore and a flexible membrane disposed over one end of the casing and is affixed to the housing so that the membrane of the casing communicates with the fluid in the cavity of the device. The bore is then pressurized to a reference pressure, this reference pressure being substantially equal to the pressure of the fluid in the device cavity. The reference pressure is then measured and the bore is vented to a pressure substantially lower than the pressure of the fluid in the chamber of the device The bore is then re-pressurized, remeasured, and revented so as to give a continuous readout.

The above noted and other objects and advantages of the invention will become more apparent from a detailed description of preferred embodiments when read in conjunction with the drawings.

BRIEF DESCRIPTION OF THE DRAWINGS

In order that the present invention may be more fully understood, it will be described, by way of example, with reference to the accompanying drawings in which:

FIG. 1A—is a perspective view of the device in cross-section;

FIG. 1B—is a view of a preferred embodiment of the device in cross-section;

FIG. 2—is a cross-sectional perspective view of a device having a membrane;

FIG. 3—is a cross-section of a device showing the position of a pressure sensing switch;

DESCRIPTION OF THE PREFERRED EMBODIMENTS

Figure 4:
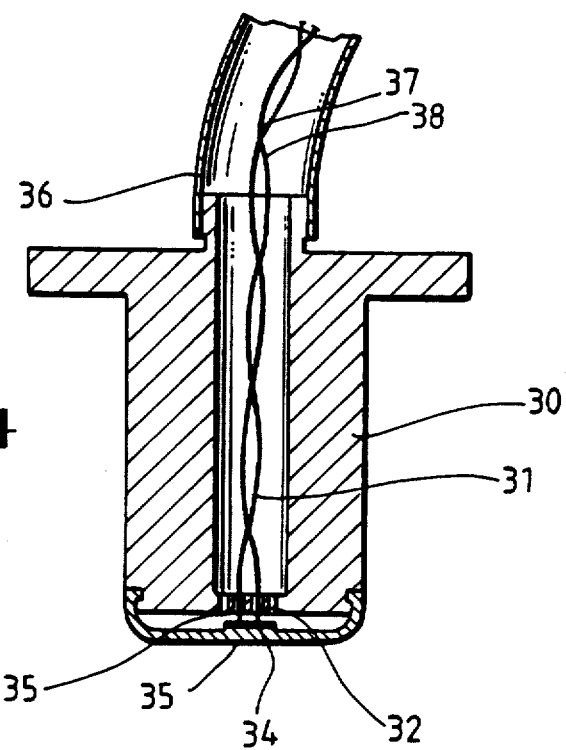
FIG. 4—is a cross-section of a pneumoelectronic switch usable with the present invention.

Referring now to the drawings, particularly to FIG. 1A, there is illustrated a perspective cross-sectional view of a sensing device housing 10. The housing is constructed of a rigid material, such as plastic, and has a base end 11 adapted to engage a cranium. There is an opening 12 at the base end and an aperture 13 adapted to receive means for sensing pressure In a preferred embodiment, the aperture is located opposite the base end opening near the top end of the housing. In an additional preferred embodiment exemplified by FIG. 1B, the housing is of a domed shape and has certain dimensions: the outside base diameter is about 45 mm; the diameter of opening 12 is about 35 mm; the distance from a plane defining opening 12 to aperture 13 is approximately 15 mm; the distance from aperture 13 to the top of collar 14 (described below) is approximately 10 mm; and the distance from the plane defining opening 12 to the top of collar 14 is approximately 25 mm.

The preferred embodiment shown by FIG. 1A includes an external collar 14 surrounding and extending distally from aperture 13 and defining a port 15 into which a pressure sensing device may be inserted. Also included is a retainer cap 16 having an annular side wall 16a and a top 16b extending radially inward to define an opening in the retainer cap. Additionally, in the embodiment shown, the external walls of collar 14 are provided with threads designed to cooperate with threads provided on the internal surface of the annular side walls of retaining cap 16. Finally, in an additional embodiment, a groove 17 will be located on the outside of the housing wall near the base end. The function of groove 17 and retainer cap 16 will be described in more detail below.

Referring now to FIG. 2, there is shown a perspective cross-section of an additional preferred embodiment of the device comprising the housing as shown in FIG. 1, with a flexible membrane 18 affixed to the base of the housing so as to seal opening 12. This membrane may be formed of a number of flexible materials, however, in a preferred embodiment, the membrane will be made of silicon. Moreover, in an additional embodiment, the membrane will be removably attached to the base of the housing with an O-ring 19 adapted to fit into groove 17. In a more preferred embodiment, the membrane will be affixed to the base with an adhesive. The membrane and housing cooperate to form cavity 20.

Referring now to FIG. 3, there is an illustration of a device wherein a pressure sensor 21 is entered into port 15 so that a projecting member of the sensor 21a rests on the upper surface of collar 14. Retaining cap 16 is then screwed on to collar 14 so as to securely sandwich the projecting member between the upper surface of the collar 14 and the inner surface of top wall 16b.

FIG. 3 also shows a suitable liquid 22, such as deionized water, medical grade silicone, etc., filling cavity 20 The liquid functions as follows: when membrane 18 is deformed, there results a change in the pressure exerted by liquid 22 on the inner surface of the housing. Since the housing is constructed of a rigid material with the exception of flexible membrane 18, pressure on membrane 18 will seek to compress liquid 22. However, since liquid 22 is relatively incompressible, it will exert pressure on the element of the pressure sensor means 21b in communication with the liquid This pressure may then be detected by pressure sensor 21.

Although various types of pressure sensors known in the art could be used with the device of FIGS. 1A & 1B, 2, and 3, (for example, Gould Statham, Cumins Fiberoptic or Hewlett-Packard transducers) FIG. 4 illustrates a preferred pressure sensor, pneumoelectric switch described in U.S. Pat. No. 4,312,361 (incorporated herein by reference). This device generally includes a rigid casing 30 defining a hollow bore 31 and having a shelf-like projection 32 extending radially into the bore at a location near the base of casing 30. A relatively fluid-impermeable switch membrane 33 is disposed over the base of the casing to seal the base end of the bore. The device contains a pair of contact electrodes 34, 35 with an electrical lead 37, 38 connected to each electrode. The electrodes will be positioned face-to-face and generally, electrode 34 will be affixed to the switch membrane while electrode 35 will be located on the lower surface of projection 32. Flexible tubing 36 is connected to casing 30 to provide fluid flow into bore 31 and also to serve as an enclosure through which electrical leads 37, 38 extend so that proper connection can be made to pressure monitor which will be described in slightly more detail below. Electrodes 34, 35 maintain contact with each other in so long as the pressure applied to the external surface of switch membrane 33, i.e., the liquid pressure in cavity 20, equals or exceeds internal pressure within bore 31. The internal pressure within bore 31 is hereinafter referred to as the "reference pressure" for reasons that will become apparent below.

The contacting electrodes serve as a closed switch signaling the pressure monitor to cause fluid to be supplied through tubing 36 into bore 31. Internal pressurization of the system occurs until the pressure in bore 31 is about equal to the pressure exerted on the external surface of membrane 33. The switch then opens (contacts 34, 35 separate) and the pressure monitor measures the reference pressure and causes bore 31 to be vented to atmosphere. Upon such venting, if pressure is applied to the external surface of switch membrane 33, electrodes 34, 35 will once again come in contact with each other, thereby causing the cycle to repeat itself By turning to FIG. 5, one can envision a preferred embodiment of the complete monitoring system. In this embodiment, a Codman CPM 100 pressure monitor 40 is used. This monitor comprises a pump for pressurizing the system, a mechanism to measure and display the reference pressure, and a mechanism for venting bore 31. With the preferred embodiment of this system, cycling can occur at 10–20 times per second, thus providing an almost continuous readout. Of course, other pressure monitors in association with appropriate transducers may be used as well.

Figure 5:
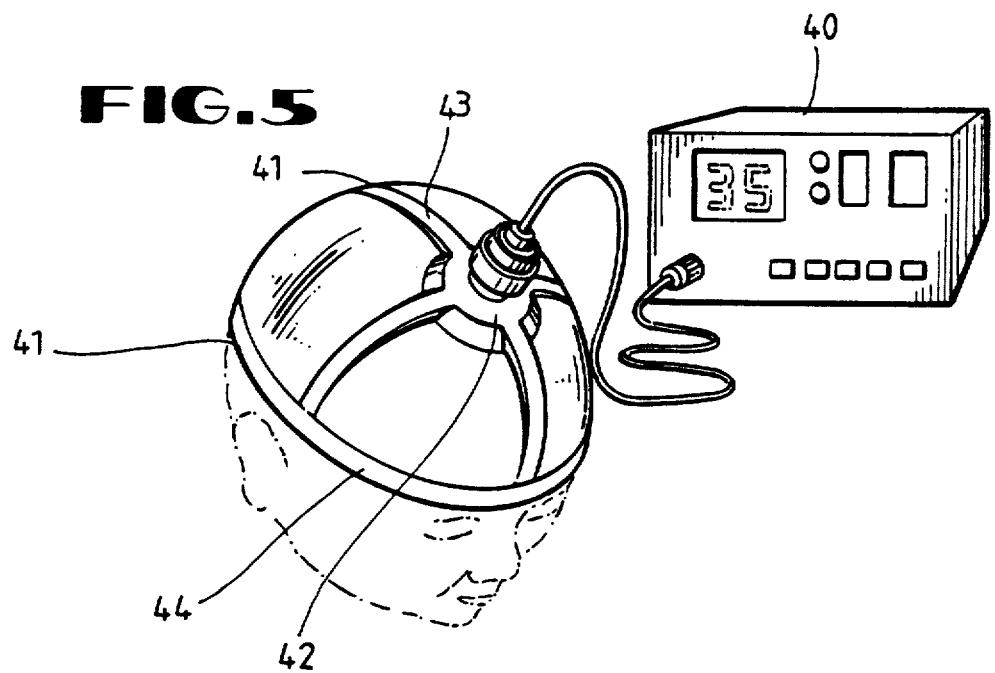
FIG. 5—illustrates an assembled anterior fontanelle monitor (AFM) monitoring system and also illustrates a preferred manner of attaching the device to the cranium.

FIG. 5 also illustrates one preferred method for mounting the device on the cranium of an infant. In this preferred embodiment, the device is affixed to the cranium with harness 41. Preferably, the harness has a central device retaining ring 42 made of a flexible plastic material and adjustable elastic straps 43 attachable to an adjustable VELCRO ® headband 44 which can be tightened or loosened to accommodate the size of the cranium of any particular infant. Of course, other suitable materials may be used to construct the harness and other strap arrangements may be used. Moreover, in certain embodiments of the invention, other types of harnesses may be used or the device may be attached with alternate methods such as surgical tape, elastic bandages, etc.

The following examples are designed to illustrate the present invention but should not be construed as limiting the scope of the claims thereof.

EXAMPLE I

A. TESTING OF THE ANTERIOR FONTANELLE PRESSURE MODEL ON A SIMULATED INFANT CRANIUM

The failure of the previous anterior fontanelle transducer designs may have been the result of inconsistent application of the principals governing pressure measurement, pressure/volume relationships and material properties of the skin. Therefore, the present inventors developed a bench model of the anterior fontanelle, referred to herein as the infant cranial model, to put these three areas into appropriate perspective. Although the magnitude of the infant cranial model's responses were found to be somewhat different from those of an actual infant cranium, the direction of change in response to simulated intracranial pressure was found to be similar. Therefore, the model provided insight into the pressure/ volume relationship and the effect of simulated intracranial pressure on fontanelle membrane distortions. It also provided direction for establishment of a standard reference frame from which anterior fontanelle pressure measurements could be made and aided in the evaluation of the anterior fontanelle monitor (AFM). The model was constructed as follows.

Circumferential measurements of the neonatal head at the level of the forehead, as well as the dimensions of the anterior fontanelle were made in seventeen babies, ranging in age from one to 42 days. Using the mean dimension for head circumference, 36.0±0.9 cm, and anterior fontanelle, 32.8±10.7 mm×20.7±9.7 mm, a latex mold of the upper portion of the neonatal head was prepared. Plaster castings were made from the mold, and the frontal, parietal, and occipital "bone" sections were bonded together at the suture lines with silicone adhesive. The assembled skull section was then bonded to a plexiglass platform to produce a hollow chamber. A thin silicone membrane was attached to the borders of the simulated anterior fontanelle opening and a mixture of clear silicone elastomer was poured over the preparation to simulate skin. After the silicone had completely cured, a small hole was drilled into the plexiglass base under the cranial model. Pressure tubing was attached to this opening to permit pressurization of the model cranial vault. Measurements of fontanelle membrane deformation and cranial bone/fontanelle membrane interface movement were made by placing the neonatal cranial model into a stereotactic frame and recording positional changes of the model fontanelle area with respect to changes in pressure (simulated intracranial pressure) within the cranial model.

B. CONSTRUCTION OF A PROTOTYPIC DEVICE

Using the mean dimensions obtained from the infant anterior fontanelle measurements, a housing was constructed in the form of a dome having an opening at one end adapted to engage an infant cranium. The outside base diameter of the dome was 45.0 and the diameter of the opening was 35.0 mm. The inside height of the dome was approximately 15 mm, as measured from its base to an aperture in the apex. A collar adapted to receive a pneumoelectronic switch surrounded the aperture and extended about 10 mm from the point where it joined the housing. Thus, the device measured about 25 mm from its base to the distal end of the collar. A thin silicon membrane was bonded to the base of the dome, thus forming a cavity adapted to receive a reference fluid. The completed chamber was placed on a flat surface and filled with deionized water.

A pneumoelectronic switch was chosen as the pressure sensor and powered by a Codman CPM 100 pressure monitor (FIG. 5). The pneumoelectronic switch was inserted into the collar, thus permitting excess water to overflow out of the chamber.

The switch functions as follows. Pressure applied externally to the pneumoelectronic switch membrane causes the switch contacts to close, in turn activating the pressure monitor to pressurize a bore in the switch body. Internal pressurization of the bore occurs until the switch contacts open. A transducer located within the CPM 100 measures the balance or reference pressure and displays it digitally. The system is then vented to atmosphere until the pneumoelectronic switch contacts close. Re-pressurization follows until the contacts are again open and an updated pressure is displayed. Cycling occurs at 10 to 20 times per second providing an almost continuous readout. Output is linear to 100 mmHg with less than 1% full scale hysteresis.

In addition, zero drift is less than 0.30 mmHg per hour and frequency response is flat to 4.0 Hz (240 cycles per minute).

The pneumoelectronic switch, as the active pressure sensing element, offers the advantage of in situ zeroing and calibration. Since the pneumoelectronic switch only senses whether or not there is pressure and is used for activating an internal reference pressure source, it can be cut out of the pneumatic and electronic circuits during zeroing and calibration without affecting the pressure transducer or its own function as a pressure sensing switch. After the transducer is rezeroed and recalibrated, the pneumoelectronic switch can be reconnected to the system and monitoring continued.

The completed AFM (FIG. 5) was calibrated and tested for linearity, hysteresis, frequency response, and zero drift. Monitor calibration was achieved by placing the device onto a hard flat surface and setting zero with the CPM 100 in the zero mode. Gain was adjusted by switching the CPM 100 into the system check mode where a 20 mmHg pressure was generated internally and applied to the transducer. Following gain adjustment, the CPM 100 was switched to the monitor mode and output was rezeroed using a bias zero adjustment. Following attachment of the device, periodic checks at the baseline were made by switching the CPM 100 into the zero mode and adjusting zero with the zero control.

Figure 6A:
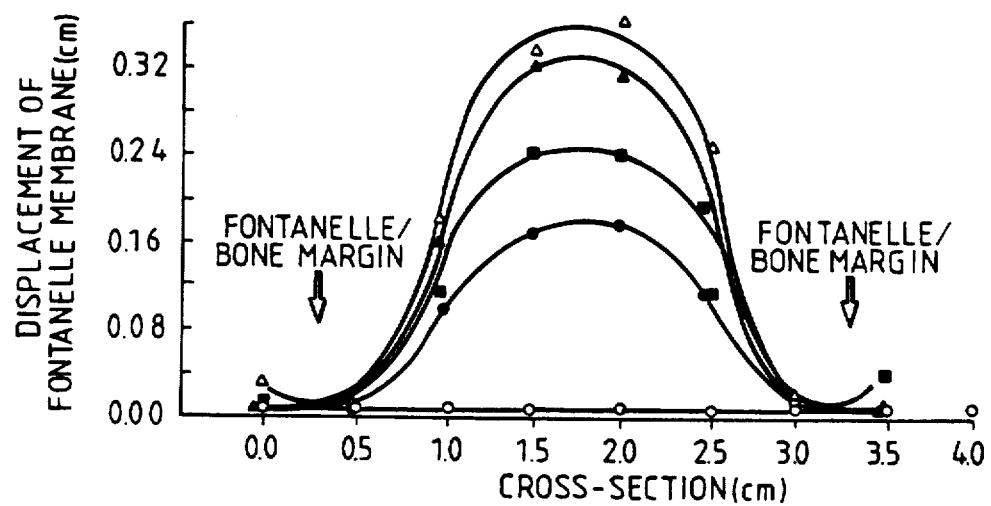
FIG. 6—depicts sagittal and coronal profiles of the anterior fontanelle membrane of the neonatal cranial model at various intracranial pressures(○=0 millimeter Hg; ) ● =10 millimeter Hg; ■ =20 millimeter Hg; ▲=30 millimeter Hg; and (Δ=40 millimeter Hg.
Figure 6B:
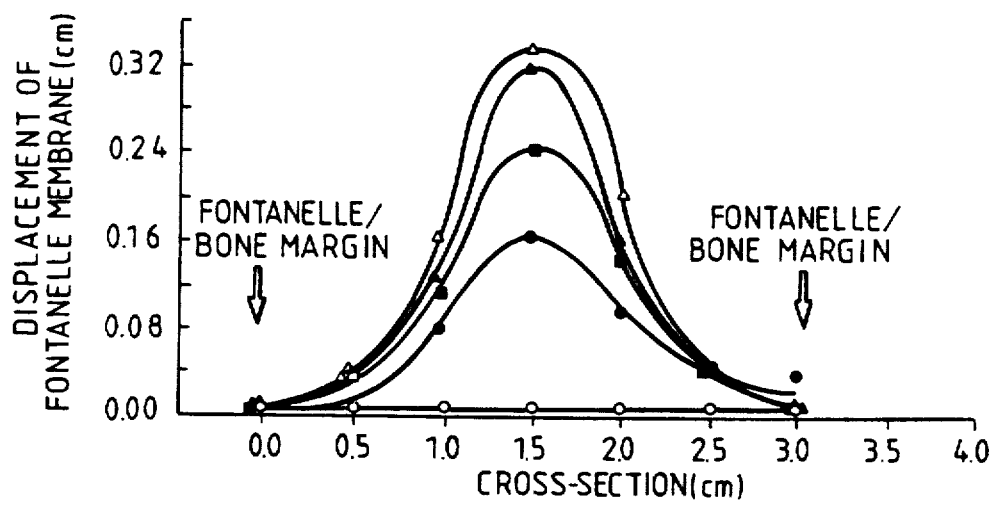

Following repeated pressurization of the model neonatal cranium, it was noted that positive simulated intracranial pressure always produced a fontanelle membrane bulge, while negative simulated intracranial pressure always produced a fontanelle depression, and zero simulated intracranial pressure resulted in the fontanelle membrane lying flat and parallel to the plane described by the edges of the cranial bones that form the fontanelle (FIG. 6).

It was also observed that the extent of simulated fontanelle membrane deformation was not linearly proportional to the simulated intracranial pressure up to 40 mmHg (FIG. 6). This finding was probably due to the nonperfect elasticity of the model's anterior fontanelle membrane since the area around and adjacent to the fontanelle membrane appeared to remain in a stable orientation over the range of simulated intracranial pressures studied (FIG. 6).

The AFM monitor was observed to be highly linear to at least 40 mmHg, with an average hysteresis of ±0.15 mmHg. Frequency response also appeared to be flat to 80 cycles per minute with a baseline drift of 0.27±0.03 mmHg per hour.

C. EVALUATION OF METHODS FOR ATTACHMENT OF THE DEVICE

Three methods for applying the assembled device to the model cranium were evaluated. The device was first attached to the model cranium over the fontanelle with surgical adhesive so that the outside edge of the base was firmly resting on the silastic "tissue" adjacent to the fontanelle. The second method held the device in position using a flexible plastic harness having adjustable elastic straps which attached to an adjustable VELCRO ® head band wrapped snugly around the base of the cranial model. For both attachment techniques, the cranial model was pressurized to various levels and the AFM output was recorded. Third, as a reference, the cranial model was fixed into a stereotactic frame and the device was positioned over the anterior fontanelle and held securely to the model cranium by the mechanical pressure of a micromanipulator, to insure no movement throughout the simulated intracranial pressure range. Prolonged monitoring of fontanelle pressure from the model cranium for each of the attachment methods was carried out in order to assess output drift. With each attachment method, the device was found to be correctly positioned when no further changes in output occurred with increased attachment tension.

Figure 7:
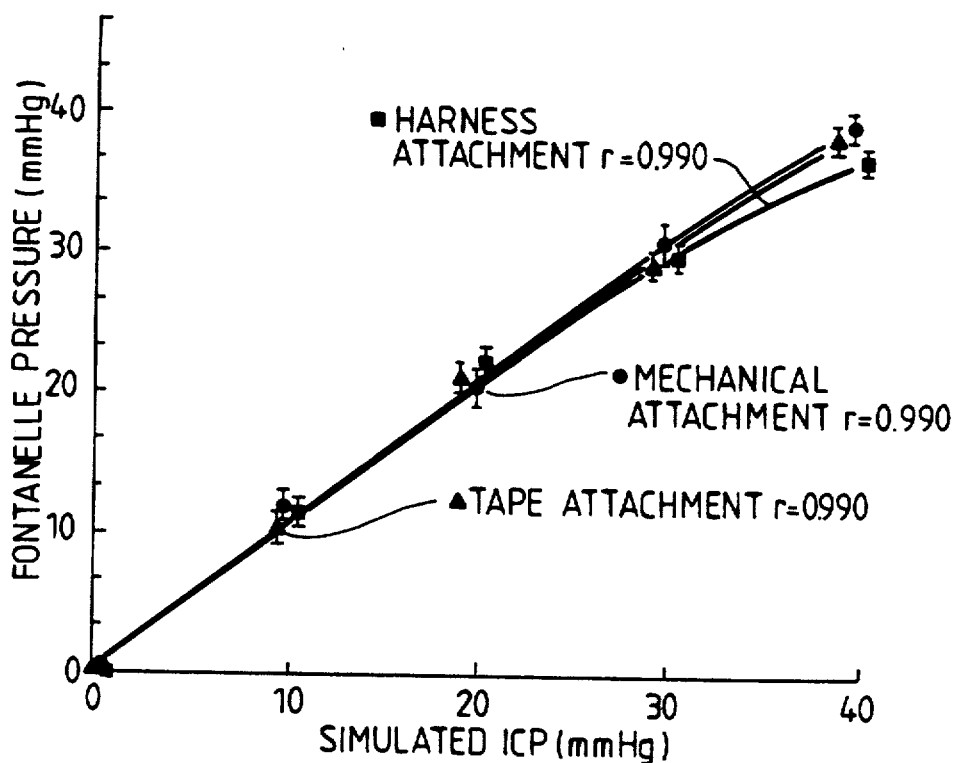
FIG. 7—is a comparison of anterior fontanelle pressure transducer output as a function of attachment techniques to the neonatal cranial model.
Figure 9:
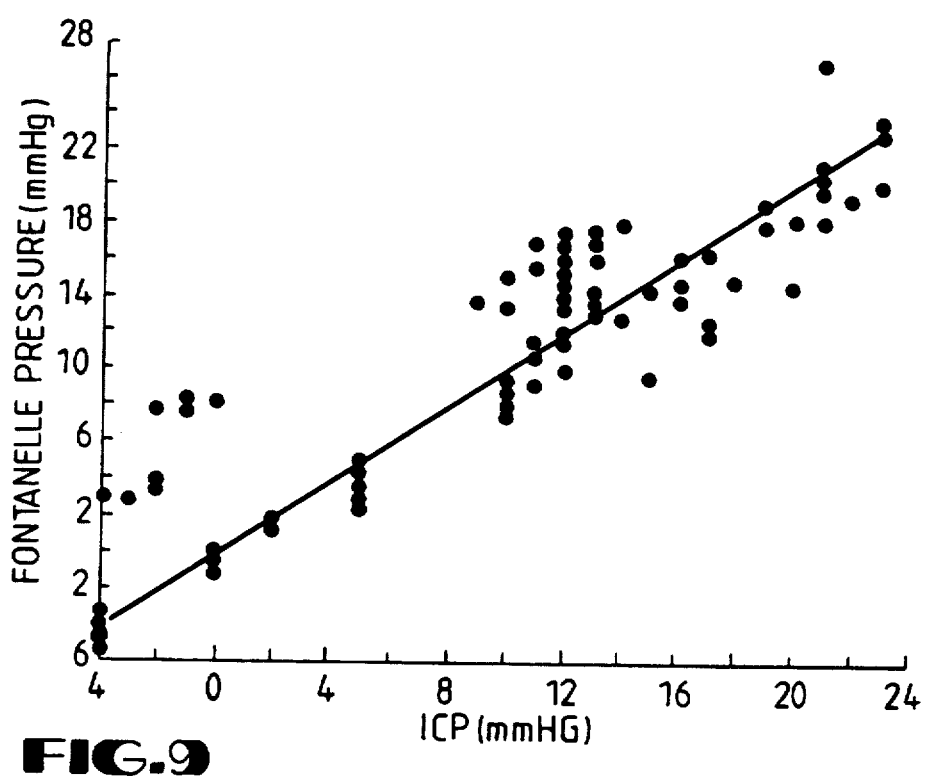
FIG. 9—least squares fit of all anterior fontanelle pressure versus ventricular intracranial pressure data obtained from three ICU neonates previously instrumented for ventricular intracranial pressure indicates significant correlation between anterior fontanelle pressure and intracranial pressure using the pneumoelectric switch. AFM correction is significant at a confidence level of 95% or better.

The three methods of device attachment (mechanical, tape, and harness) that were studied produced highly linear outputs highly correlated with the simulated intracranial pressure up to 30 mmHg. (FIG. 7) At pressures above 30 mmHg, the output from systems employing mechanical and tape attachment techniques showed a slight deviation from linearity, while output from a system employing the harness attachment was consistently lower by approximately 7.5% than the simulated intracranial pressure at 40 mmHg. AFM output drift as a function of application technique indicated that for the mechanical and harness attachments, drift is within the same range as the baseline drift of the AFM, 0.27±0.03 mmHg per hour and 0.20+ 80 mmHg per hour.

TABLE I

| Application Technique | Drift Rate |
|---|---|
| Mechanical | 0.27 ± 0.03 mmHg/hr |
| Tape | 2.10 ± 0.80 mmHg/hr |
| Harness | 0.20 ± 0.20 mmHg/hr |

Therefore, AFM output for all attachment techniques varied somewhat with application pressure and it was noted that an application pressure greater than the simulated fontanelle pressure was necessary for AFM output to correlate with simulated intracranial pressure. Sufficient application pressure was easily attained by increasing tension in the tape or harness straps until no further change in anterior fontanelle pressure was noted.

Application techniques used with the devices of the prior art vary: most involve the use of adhesive mediums. The experience of the present inventors indicates that these techniques are useful only for applications of short duration since significant drift was noted in the transducer output with their use. Adhesives tend to slip over time and in combination with gradual tape stretching, invariably lead to lower estimates of intracranial pressure. The use of elastic bandages may reduce the component of output drift due to material relaxation, however, the adhesive slippage component may still introduce significant error into the intracranial pressure estimate. Transducer attachments utilizing a harness with elastic straps appear to provide adequate application pressure over a wide range of simulated intracranial pressures in the infant cranial model, and accurate estimates of simulated intracranial pressure have been measured repeatedly in this cranial model.

EXAMPLE II

A. EVALUATION WITH LIVING INFANTS

The AFM was also evaluated in three infants. One was six months of age with cryptococcus meningitis; the second, nine months with head trauma; and the third, ten months with a brain tumor. Each infant was also monitored by a ventricular catheter. The device was applied to the anterior fontanelle without the evaluator's knowledge of the ventricular intracranial pressure and followed for up to 80 minutes. A regression analysis and correlation calculation was performed on the data and a scatter plot of anterior fontanelle pressure versus ventricular intracranial pressure was generated.

Figure 8A:
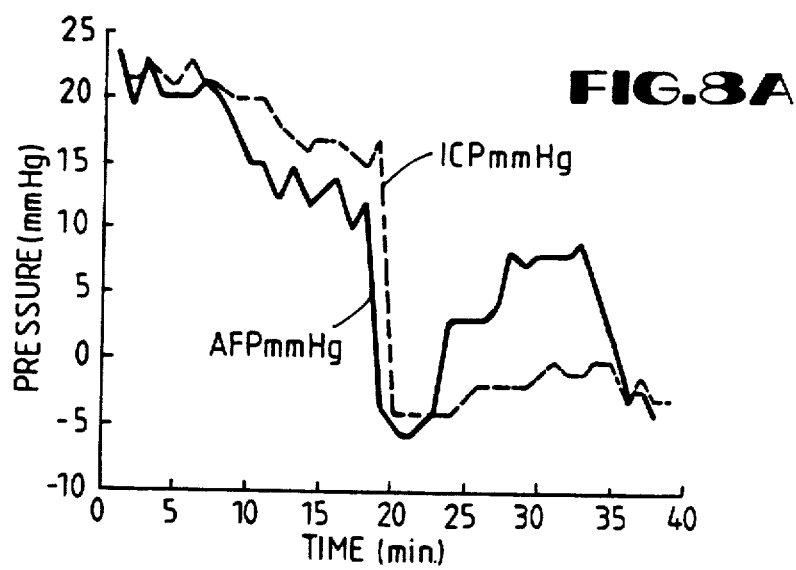
FIG. 8—is time course plots for anterior fontanelle pressure and ventricular catheter pressure in three ICU neonates previously instrumented for ventricular intracranial pressure.
Figure 8B:
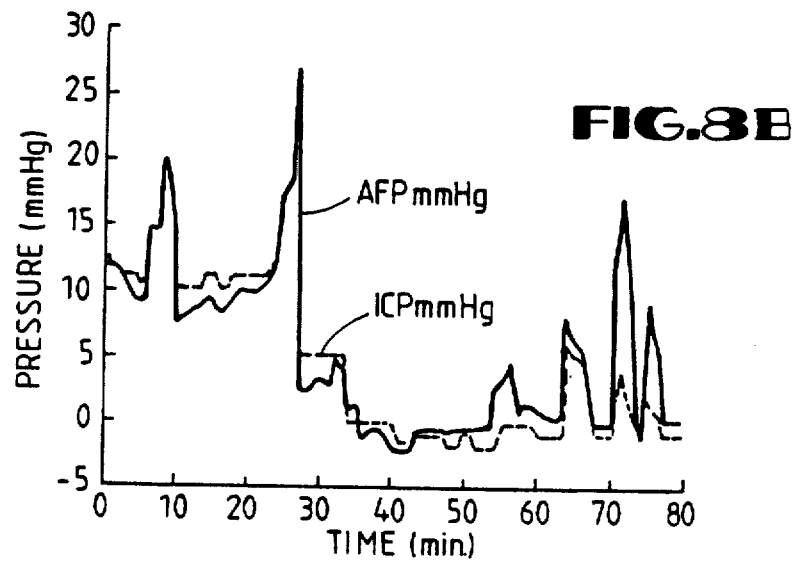
Figure 8C:
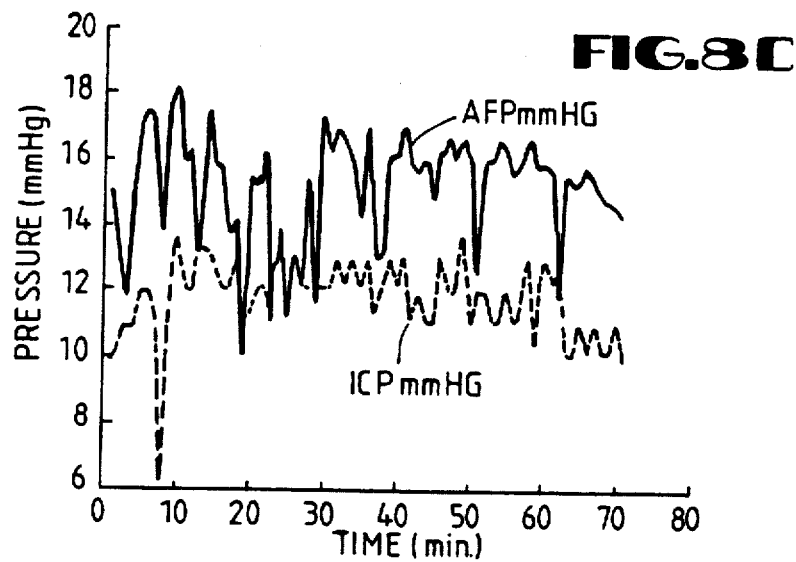

These results showed device application using the harness attachment was uncomplicated and generated reproducible results. (FIG. 7) Anterior fontanelle pressure was higher than intracranial pressure measured with the ventricular catheter by an average of $3.4 \pm 1.4\%$. The AFM system tracked positive and negative intracranial pressure very well, with pressure rising more rapidly and reading consistently higher than pressure measured with the ventricular catheter. (FIG. 7) The relationship between anterior fontanelle pressure and intracranial pressure was highly correlated ($R = 0.962$) at a confidence level greater than 95%. Variability was greater at the lower pressures than at the higher pressures. (FIG. 8) Importantly, no sensitivity to patient motion was noted.

Therefore, blind applications of the device to the anterior fontanelle of three different patients already instrumented with ventricular catheters followed by measurement of intracranial pressure with the AFM system resulted in intracranial pressure estimates that were similar to the ventricular catheter pressures. (FIG. 8) Furthermore, the AFM employing the novel pressure device described in the present application appears to have a better frequency response than the ventricular catheters to which it was compared. Catheter damping, the result of catheter tip obstruction or accidental introduction of air into the pressure lines, is avoided with the AFM. The AFM can also be used together with, or following removal of, the ventricular cannula and maintained indefinitely without risk of infection. Also, patient movement and positional changes do not appear to affect AFM output.

B. CONCLUSIONS

In general, intracranial pressure can be perceived as the result of CSF and/or the brain exerting a force onto the inner table of the skull. Non-rigid areas, such as the anterior fontanelle in the cranial vault will be visibly deformed in proportion to the force applied to this area. With respect to atmospheric pressure, a positive intracranial pressure will cause a fontanelle bulge while a negative intracranial pressure will cause a fontanelle concavity. Zero intracranial pressure with respect to the atmosphere results in the anterior fontanelle membrane lying flat within the plane of the scalp.

Although transducer designs utilizing fontanelle deformation or fontanelle tension as a basis for estimating intracranial pressure may be subject to some error resulting from non-uniform elasticity of skin due to varying levels of hydration, nutrition, and temperature, the present inventors have shown that accurate estimates of intracranial pressure can be made if transcutaneous compression of the fontanelle membrane is minimized and the cranial bones forming the fontanelle are relatively firmly attached to one another. Then, the pressure applied to the intracranial side of the anterior fontanelle membrane is transmitted extracranially by the membrane with little attenuation, and a pressure sensing device firmly attached to the scalp overlying the cranial bone margin of the anterior fontanelle has about the same pressure exerted onto its membrane as is exerted onto the inner table of the scalp by the intracranial contents. In essence, the scalp overlying the cranial bone margin of the anterior fontanelle acts as a stable reference point from which reliable estimates of intracranial pressure can be made. Of course, in some cases, accurate estimates of intracranial pressure from the anterior fontanelle may also depend on other variables, for example, the cross-sectional diameter of the device, position on the anterior fontanelle, application pressure, and attachment technique.

It is certainly important that the base of the device have sufficient diameter so that its outer edges will rest on the area beyond the anterior fontanelle membrane-cranial bone interface. This provides a consistent and stable reference from which measurement can be made. It is also important that the device be positioned directly over the apex of the anterior fontanelle. Positions which are skewed may result in inconsistent referencing and transmission of pressure to the flexible membrane.

Following positioning, sufficient pressure must be applied to the device to insure firm contact with the bony fontanelle margins. In the infant cranial model, sufficient application pressure was applied when further increases in application pressure resulted in no further changes in monitor output. With insufficient application pressure, the anterior bulge prevents the base of the device from contacting the reference points and lower estimates in intracranial pressure may occur. Excessive application pressure does not significantly affect intracranial pressure estimates in the infant cranial model when cross-sectional diameter of the device is sufficiently large to allow contact with the scalp adjacent to the bony margin of the fontanelle. However, in humans when application pressure is excessive, damage to tissue at the contact sites may result from decreased tissue perfusion. The present inventors have found that application pressure slightly higher than the actual intracranial pressure is necessary for accurate estimations of intracranial pressure from the fontanelle.

The present invention has been disclosed in terms of specific embodiments believed by the inventors to be the best mode for carrying out the invention. However, in light of the disclosure herein provided, those of skill in the various arts will recognize that modifications can be made without departing from the intended scope of the invention. Accordingly, these and all modifications are considered to be within the scope of the appended claims.

What is claimed is:

1. A pressure sensing device comprising:
   rigid housing having a base end and an end opposite said base end, said base end defining an opening adapted for engaging a cranium of an infant circumferential to the anterior fontanelle and said opposite end defining an aperture adapted to receive means for sensing pressure.

2. A device for sensing pressure at the anterior fontanelle, comprising a rigid housing having a base end adapted for engaging a bony cranium of an infant circumferential to the anterior fontanelle, an opening at said base end adapted for receiving a membrane adapted to engage the skin of an infant overlying the anterior fontanelle, and an aperture in said housing for receiving means for sensing pressure.

3. The device of claim 1 or claim 2 further comprising:
   a flexible membrane disposed over the opening and adapted for engaging an anterior fontanelle; and
   the housing and membrane cooperating to define a cavity adapted to receive a fluid.

4. The device of claim 3 further comprising:

a fluid filling the cavity; and means for detecting fluid pressure changes within the cavity.

5. The device of claim 1 or claim 2 wherein the opening has a diameter of about 35 mm.

6. The device of claim 1 or claim 2 wherein the housing has walls about 5 mm thick defining the opening.

7. The device of claim 1 or claim 2 wherein the distance from a plane defined by the base end of the housing to the aperture is about 15 mm.

8. The device of claim 1 or claim 2 wherein the housing is formed of a plastic material.

9. The device of claim 1 or claim 2 wherein the housing has a domed shape.

10. The device of claim 1 or claim 2 wherein the circumference of the opening at the base end is equal to or greater than the circumference of an infant fontanelle.

11. The device of claim 1 or claim 2 wherein the aperture is positioned opposite the opening of the base end.

12. The device of claim 1 or claim 2 wherein the aperture comprises:
 (a) an external collar defining a port;
 (b) a retainer cap having an annular side wall and a top wall extending radially inward to define an opening in the cap; and
 (c) means for engaging the outer surface of the collar with the inner surface of the annular wall of the retainer cap so as to facilitate sandwiching a member of a pressure sensing means between the upper surface of the collar and the internal surface of the top wall of the retainer cap.

13. The device of claim 1 or claim 2 further comprising means for mounting the housing on the head of an infant.

14. The device of claim 13 wherein the means comprises a harness having elastic straps.

15. The device of claim 3 wherein the flexible membrane comprises a silicon membrane.

16. The device of claim 3 wherein the flexible membrane is affixed to the housing with an adhesive.

17. The device of claim 3 further comprising an O-ring adapted for attaching the membrane to the housing.

18. The device of claim 4 wherein the fluid comprises an incompressible fluid.

19. The device of claim 18 wherein the fluid comprises an aqueous fluid.

20. The device of claim 18 wherein the fluid comprises liquid silicone.

21. The device of claim 4 wherein the pressure sensing means comprises a pneumatic switch.

22. The device of claim 4 wherein a pressure sensing element of the pressure sensing means is disposed in the aperture in the housing to communicate with the fluid in the cavity.

23. A method for measuring intracranial pressure comprising:
 (a) providing a pressure sensing device enclosing a fluid-filled cavity said device having a rigid housing with a flexible membrane window and means for sensing pressure communicating with the fluid in the cavity;
 (b) applying the device to the cranium of an infant in a manner such that the flexible membrane lies adjacent to the skin covering the anterior fontanelle, the rigid housing is supported by the cranium, and deformation of the skin covering the fontanelle causes a corresponding deformation of the flexible membrane and thereby changes the fluid pressure within the cavity; and
 (c) detecting the fluid pressure change within the cavity with the pressure sensing means.

24. The method of claim 23 further comprising:
 (a) providing pressure sensing means having a rigid casing defining a bore and a flexible sensor membrane disposed over one end of the casing;
 (b) affixing the pressure sensing means to the housing so that the sensor membrane communicates with the fluid in the cavity of the device;
 (c) pressurizing the bore to a reference pressure, said reference pressure being substantially equal to the pressure of the fluid in the device cavity;
 (d) measuring the reference pressure;
 (e) venting the bore to a pressure substantially lower than the pressure of the fluid in the cavity of the device; and
 (f) repeating steps (c)–(e).

25. The method of claim 23 wherein the device is applied to the cranium with a harness having elastic straps.

* * * * *

UNITED STATES PATENT AND TRADEMARK OFFICE
CERTIFICATE OF CORRECTION

PATENT NO. : 4,995,401
DATED : February 26, 1991
INVENTOR(S) : Bunegin et al.

It is certified that error appears in the above-identified patent and that said Letters Patent is hereby corrected as shown below:

In column 2, line 30, please insert a period between the words "reported" and "Therefore,".

In column 3, line 27, please replace "shown in FIGS. IA" with --shown in FIGS. 1A--.

In column 3, line 29, please replace "and IB, 2 or 3" with --and 1B, 2 or 3--.

In column 3, line 53, please insert a period between the words "obtained" and "Of".

In column 4, line 14, please insert a period between the words "membrane" and "In".

UNITED STATES PATENT AND TRADEMARK OFFICE
CERTIFICATE OF CORRECTION

PATENT NO. : 4,995,401
DATED : February 26, 1991
INVENTOR(S) : Bunegin et al.

It is certified that error appears in the above-identified patent and that said Letters Patent is hereby corrected as shown below:

In column 4, line 15, please insert a period after the word "adhesive".

In column 4, line 20, please insert a period between the words "cavity" and "As".

In column 4, line 28, please insert a period between the words "pressure" and "In".

In column 4, line 40, please insert a period between the words "pressure" and "This".

In column 4, line 43, please insert a period between the words "pressure" and "The".

UNITED STATES PATENT AND TRADEMARK OFFICE
CERTIFICATE OF CORRECTION

PATENT NO. : 4,995,401

DATED : February 26, 1991

INVENTOR(S) : Bunegin et al.

It is certified that error appears in the above-identified patent and that said Letters Patent is hereby corrected as shown below:

In column 4, line 65, please insert a period between the words "device" and "The".

In column 5, line 27, please replace "Hg; ) ● = 10" with --Hg; (●) = 10--.

In column 5, line 27, please replace "Hg; ■ = 20" with --Hg; (■) = 20--.

In column 5, line 28, please replace "▲ = 30" with --(▲) = 30--.

In column 5, line 28, please replace "and (Δ = 40" with --(Δ) = 40--.

UNITED STATES PATENT AND TRADEMARK OFFICE
CERTIFICATE OF CORRECTION

PATENT NO. : 4,995,401
DATED : February 26, 1991
INVENTOR(S) : Bunegin et al.

It is certified that error appears in the above-identified patent and that said Letters Patent is hereby corrected as shown below:

In column 5, line 53, please insert a period between the words "pressure" and "In".

In column 6, line 41, please insert a period between the words "liquid" and "The".

In column 7, line 16, please insert a period after the word "itself".

In column 10, line 22, please replace the words "and $0.20^+ 80$ mmHg" with --and $0.20^+ 0.80$ mmHg--.

UNITED STATES PATENT AND TRADEMARK OFFICE
CERTIFICATE OF CORRECTION

PATENT NO. : 4,995,401
DATED : February 26, 1991
INVENTOR(S) : Bunegin et al.

It is certified that error appears in the above-identified patent and that said Letters Patent is hereby corrected as shown below.

In column 12, line 48, please replace the words "rigid housing" with --a rigid housing--.

Signed and Sealed this

Eleventh Day of August, 1992

Attest:

DOUGLAS B. COMER

Attesting Officer

Acting Commissioner of Patents and Trademarks